United States Patent [19]

Miyashita et al.

[11] 4,248,870

[45] Feb. 3, 1981

[54] MAYTANSINOIDS AND USE

[75] Inventors: Osamu Miyashita, Osaka; Hiroshi Akimoto, Hyogo, both of Japan

[73] Assignee: Takeda Chemical Industries, Ltd., Osaka, Japan

[21] Appl. No.: 85,880

[22] Filed: Oct. 18, 1979

[51] Int. Cl.³ .................. A61K 31/535; C07D 498/16
[52] U.S. Cl. ........................ 424/248.54; 260/239.3 P
[58] Field of Search ........................... 260/239.3 P; 424/248.54

[56] References Cited

U.S. PATENT DOCUMENTS

| | | | |
|---|---|---|---|
| 3,896,111 | 7/1975 | Kupchan et al. | 260/239.3 P |
| 4,137,230 | 1/1979 | Hashimoto et al. | 260/239.3 P |
| 4,162,940 | 7/1979 | Higashide et al. | 260/239.3 P |

OTHER PUBLICATIONS

Kupchan et al., "J. Med. Chem.", vol. 21, No. 1, pp. 31–37 (1978).

Primary Examiner—Henry R. Jiles
Assistant Examiner—Robert T. Bond
Attorney, Agent, or Firm—Davis, Miller & Mosher Stevens

[57] ABSTRACT

Novel maytansinoids of the formula:

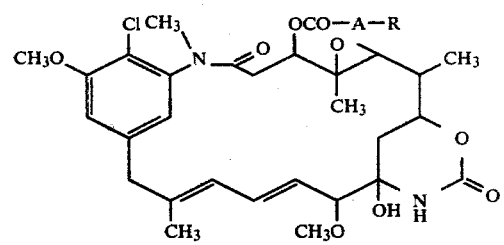

wherein
R is an alicyclic hydrocarbon group of 3 to 10 carbon atoms, phenyl or heterocyclic group, which may optionally be substituted, and
A is an alkylene group of 1 to 4 carbon atoms or a bond, provided that A means said alkylene group when attached to a N atom in said heterocyclic group R,
have antimicrobial, antimitotic and antitumor activities.

13 Claims, No Drawings

MAYTANSINOIDS AND USE

This invention provides maytansinoid compound of the following formula (I):

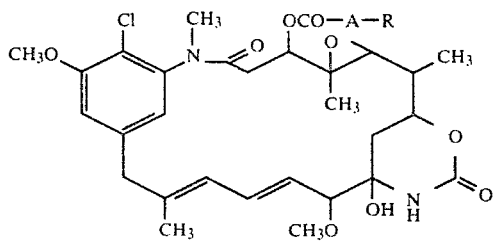

wherein R is an alicyclic hydrocarbon group of 3 to 10 carbon atoms, phenyl or heterocyclic group, which may optionally be substituted; and A is an alkylene group of 1 to 4 carbon atoms or a bond, provided that A means said alkylene group when attached to a N atom in said heterocyclic group R, and a method for production and use of the compounds (I).

Referring to the above formula (I), the alicyclic hydrocarbon group of 3 to 10 carbon atoms as designated by the symbol R may for example be a cycloalkyl group (e.g. cyclopropyl, cyclobutyl, cyclopentyl, cyclohexyl, cycloheptyl, cyclooctyl, norbornyl, adamantyl, etc.) or a cycloalkenyl group (e.g. 1-cyclobutenyl, 1-, 2-, or 3-cyclopentenyl, 1-, 2- or 3-cyclohexenyl, 4-cycloheptenyl, 4-cyclooctenyl, 1,4-cyclohexadienyl, 4-norbornenyl, 2,4,6-cycloheptatrienyl, etc.)

As examples of the heterocyclic group R there may be mentioned 4-, 5- or 6-membered heterocyclic groups containing N, O or/and S as hetero-atoms. This heterocyclic group R may be saturated or unsaturated, and a benzene ring may be fused thereto. As examples of such N-containing 4-, 5- or 6-membered heterocyclic groups, there may be mentioned azetidinyl, pyridyl, 1,2,3,4-tetrahydropyridyl, piperidyl, quinolyl, 1,2-dihydroquinolyl, 3- or 4-isoquinolyl, 1,2-dihydroisoquinolyl, pyrrolyl, pyrrolinyl, pyrrolidinyl, indolyl, etc.

As examples of said oxygen-containing 5- or 6-membered heterocyclic groups, there may be mentioned furyl, pyranyl, dihydropyranyl, benzofuryl, benzopyranyl, etc. The sulfur-containing 5- or 6-membered heterocyclic groups include thienyl, benzothienyl, etc.

The above-mentioned heterocyclic group may have from 2 to 4 hetero-atoms, which may be the same or different and any of N, O or/and S. As examples of such heterocyclic groups there may be mentioned imidazolyl, pyrazinyl, pyrimidyl, pyridazinyl, 2-imidazolinyl, imidazolidinyl, benzimidazolyl, indazolyl, quinoxalyl, quinazolinyl, cinnolinyl, 1,4-dioxanyl, 1,4-benzodioxanyl, 1,2- or 1,3-dithioranyl, 1,3-dithianyl, isoxazolyl, oxazolyl, morpholinyl, benzisoxazolyl, benzoxazolyl, isothiazolyl, thiazolyl, benzisothiazolyl, benzothiazolyl, benzothiazinyl, 1,2,4-, 1,2,5- or 1,3,4- oxadiazolyl, 1,2,3-, 1,2,4-, 1,2,5- or 1,3,4- thiadiazolyl, 1,2,3-, 1,2,5- or 1,3,4- triazolyl, 1,3,5-triazinyl, benzotriazolyl, tetrazolyl, etc.

Among the above-mentioned heterocyclic groups, NH-containing groups such as azetidinyl, 1,2,3,4-tetrahydropyridyl, piperidyl, 1,2-dihydroquinolyl, 1,2-dihydroisoquinolyl, pyrrolyl, pyrrolinyl, pyrrolidinyl, pyrazolyl, 2-imidazolinyl, imidazolidinyl, indazolyl, morpholinyl, 1,2,3-, 1,2,5- or 1,3,4-triazolyl, benzotriazolyl, tetrazolyl, etc. are usually preferably substituted in the particular N-position by an appropriate substituent to be described hereinafter or preferably have said alkylene group A attached to the N-position.

Any of the above-mentioned $C_{3-10}$ alicyclic hydrocarbon group, phenyl and heterocyclic group may have substituents such as alkyl groups of 1 to 4 carbon atoms (e.g. methyl, ethyl, n-propyl, isopropyl, n-butyl, isobutyl, sec-butyl, tert-butyl, etc.), alkoxy groups of 1 to 4 carbon atoms (e.g. methoxy, ethoxy, n-propoxy, isopropoxy, n-butoxy, iso-butoxy, sec-butoxy, tert-butoxy, etc.), alkanoyl groups of 2 to 4 carbon atoms (e.g. acetyl, propionyl, n-butyryl, isobutyryl, etc.), alkanoyloxy groups of 2 to 4 carbon atoms (e.g. acetyloxy, propionyloxy, n-butyryloxy, isobutyryloxy, etc.), alkoxycarbonyl groups of 2 to 4 carbon atoms (e.g. methoxycarbonyl, ethoxycarbonyl, n-propoxycarbonyl, isopropoxycarbonyl, etc.), halogen (e.g. chlorine, fluorine, bromine, iodine), nitro, cyano, trifluoromethyl, di($C_{1-4}$) alkylamino groups (e.g. dimethylamino, diethylamino, dipropylamino, diisopropylamino, dibutylamino, etc.), alkylthio groups of 1 to 4 carbon atoms (e.g. methylthio, ethylthio, n-propylthio, isopropylthio, n-butylthio, isobutylthio, sec-butylthio, tert-butylthio, etc.), methylsulfinyl, methylsulfonyl, oxo, thioxo, alkanoylamido groups of 1 to 4 carbon atoms (e.g. formamido, acetamido, propionylamido, butyrylamido, isobutyrylamido, etc.) and so on. These substituents may be the same or different and may total 1 to 3.

As examples of alicyclic hydrocarbon groups of 3 to 10 carbon atoms having such substituents, there may be mentioned 2,2-dimethylcyclopropyl, 2-propylcyclopropyl, 2-butylcyclopropyl, 4-isobutylcyclohexyl, 3,3-dimethyl-4-cyclobutenyl, 2-bromocyclopropyl, 2-chlorocyclobutyl, 4-chlorocyclohexyl, 2-iodocyclohexyl, 2,2-difluorocyclobutyl, 3-methoxycyclohexyl, 2,2-dimethyl-3-acetylcyclobutyl, 4-acetylcyclohexyl, 2-cyanocyclohexyl, 2-cyanocyclobutyl, 4-cyanocyclohexyl, 4-ethoxycarbonyl-1-cyclohexenyl, 4-butoxycarbonyl-1-cyclohexenyl, 4-dimethylaminocyclohexyl, etc. As examples of the substituted phenyl, there may be mentioned 2-, 3- or 4-methylphenyl, 4-tert-butylphenyl, 2-, 3- or 4-chlorophenyl, 2-, 3- or 4-bromophenyl, 2-, 3- or 4-iodophenyl, 2-, 3- or 4-fluorophenyl, 2- or 4-methoxyphenyl, 4-butoxyphenyl, 4-methoxycarbonylphenyl, 3-acetylphenyl, 2-, 3- and 4-nitrophenyl, 3- or 4-cyanophenyl, 4-dimethylaminophenyl, 4-diethylaminophenyl, 4-acetoxyphenyl, 4-butyryloxyphenyl, 2,4-, 2,5-, 2,6-, 3,4- or 3,5-dichlorophenyl, 3,4-dimethoxyphenyl, 3,4,5-trimethoxyphenyl, 3,4-methylenedioxyphenyl, 3-trifluoromethylphenyl, 4-methylthiophenyl, 4-methylsulfonylphenyl, 4-acetamidophenyl, etc.

As examples of said 4-, 5- or 6-membered heterocyclic group which may optionally be substituted, there may thus be mentioned 1-acetyl-2-azetidinyl, 1-methyl-2-pyrrolyl, 3-methoxy-2-furyl, 3-methyl-2-furyl, 5-methyl-2-furyl, 5-nitro-2-furyl, 3-methyl-2-thienyl, 3-bromo-4,5-dimethyl-2-thienyl, 2-methyl-4-thiazolyl, 1,2-dimethyl-4-chloro-5-imidazolyl, 1-butyl-4-pyrazolyl, 2,4-dichloro-4-isothiazolyl, 5-methyl-1,2,3-thiadiazol-4-yl, 3,5-dimethyl-4-isoxazolyl, 2-methyl-5-diisopropylamino-4-oxazolyl, 5-methyl-1,2,5-oxadiazol-3-yl, 4-methoxy-1,2,5-oxadiazol-3-yl, 5-methyl-1,3,4-oxadiazol-2-yl, 3-methyl-1,2,3-thiadiazol-5-yl, 5-methyl-1,3,4-thiadiazol-2-yl, 5-methyl-1,2,3-thiadiazol-4-yl, 1-methyl-1,2,3-triazol-4-yl, 2-ethyl-1,2,3,4-tetrazol-5-yl, 5-nitro-2-pyridyl, 6-ethyl-4-pyridyl, 5-ethoxycarbonyl-3-pyridyl, 5-chloro-3-pyridyl, 1-butyryl-2-piperidyl, 2-oxo-5-pyranyl, 7-methoxy-3,4-dihydro-2H-2-pyranyl, 1-acetyl-2-pyrrolidinyl, 1-propyl-5-oxo-3-pyrrolidinyl, 3-methyl-2,4-dioxo-5-thiazolidinyl, 4-, 5-, 6- or 7-nitro-3-indolyl, 5-fluoro-2-indolyl, 2-methyl-5-methoxy-3-indolyl, 1-methyl-2-indolyl, 5-chloro-2-benzothienyl, 3-methyl-2-benzofuryl, 1-methyl-2-benzimidazolyl, 6-nitro-2-benzothiazolyl, 4-chloro-3-quinolyl, 6-methoxy-2-quinolyl, 2,4-dimethoxy-3-quinolyl, 2-methyl-1-oxo-1,2-dihydroisoquinolyl, 7-methyl-3-cumaryl, 4-methyl-quinazolyl, 3-propyl-2,4-dioxo-5-imidazolinyl, 7-methoxycarbonyl-2-oxo-1,2-dihydro-3-quinazolyl, 2-furyl, 2-thienyl, 3-isoxazolyl, 4-imidazolyl, 1,2,5-thiadiazolyl-3-yl, 2-, 3- or 4-pyridyl, 2-pyrazinyl, 2-pyrimidinyl, 2-s-triazinyl, 1,2-dithioranyl, 3-indolyl, 2-benzothienyl, 2-benzofuryl, 3-benzopyrazolyl, 2-benzimidazolyl, 2-benzoxazolyl, 3-benzisoxazolyl, 3-benzisothiazolyl, 2-benzothiazolyl, 2-benz-1,4-oxasinyl, 3-quinolyl, 1-isoquinolyl, etc.

As examples of said N-containing heterocyclic group R having said alkylene group A attached to its N-atom (i.e. the group-A-R) there may be mentioned 1-pyrrolylmethyl, 2-oxo-1-pyrrolidinylmethyl, 1-imidazolylmethyl, 3,5-dimethyl-1-pyrazolylmethyl, 1-piperidylethyl, 4-morpholinylmethyl, 1-tetrazolylmethyl, 2,5-dioxo-1-pyrrolidinylmethyl, 1,3-dioxo-2-isoindolylmethyl, 2-thioxo-4-oxo-3-thiazolidinylmethyl, 3,5-diiodo-4-oxo-1,4-dihydro-1-pyridylmethyl, 4-methyl-1-piperazinylmethyl, 1-indolylethyl, etc.

As shown in the formula (I) presented hereinbefore, when A is an alkylene group, the group R is attached to the 3-carbonyloxy group of the same formula (I) as interrupted by said alkylene group, and when A is a bond, R is directly attached to said 3-carbonyloxy group.

The alkylene group of 1 to 4 carbon atoms as represented by the symbol A may be a straight-chain or branched group such as methylene, ethylene, methylmethylene (ethylidene), propylene, butylene, 1-, 2- or 3-methylpropylene, 1- or 2-ethylethylene, propylmethylene, 1,1- or 1,2-dimethylethylene, isopropylmethylene, etc.

Referring, further, to formula (I), where A is directly attached to a N-atom of heterocyclic group R, it represents said alkylene group of 1 to 4 carbon atoms and cannot be a bond.

In the above-mentioned compounds (I), desirable is a compound of the formula (I) wherein R is $C_{3-10}$ cycloalkyl, $C_{3-10}$ cycloalkenyl, phenyl or 4-, 5- or 6-membered heterocyclic group containing N, O or/and S which may have a fused benzene ring, said cycloalkyl, cycloalkenyl, phenyl and heterocyclic group being unsubstituted or substituted by $C_{1-4}$ alkyl, $C_{1-4}$ alkoxy, $C_{2-4}$ alkanoyl, $C_{2-4}$ alkanoyloxy, $C_{2-4}$ alkoxycarbonyl, halogen, nitro, cyano, trifluoromethyl, di-$C_{1-4}$ alkylamino, $C_{1-4}$ alkylthio, methylsulfinyl, methylsulfonyl, oxo, thioxo or $C_{1-4}$ alkanoylamido, and A is $C_{1-4}$ alkylene or a bond provided that A means said alkylene when attached to a N atom in said heterocyclic group R, and more desirable is a compound of the formula (I) wherein R is $C_{3-7}$ cycloalkyl, phenyl, 5-membered heterocyclic group containing O or S, or 5- or 6-membered heterocyclic group containing one to four of N, said cycloalkyl, phenyl and heterocyclic groups being unsubstituted or substituted by $C_{1-4}$ alkyl, $C_{1-4}$ alkoxy, $C_{2-4}$ alkanoyl or halogen, and A is $C_{1-4}$ alkylene or a bond, provided that A means said alkylene when attached to a N atom in said heterocyclic group R.

The maytansinoid compound of formula (I) can be produced by acylating maytansinol with a carboxylic acid of the formula (II):

R—A—COOH   (II)

wherein

R and A are as defined hereinbefore, or a reactive derivative of (II) with respect to the carboxyl function thereof.

An exemplary reaction procedure comprises acylating maytansinol with a carboxylic acid (II) in the presence of a carbodiimide. Based on maytansinol, carboxylic acid (II) may be used in an amount of, for example, about 1 to 500 molar equivalents and, in many cases, is preferably employed in an amount not exceeding about 30 molar equivalents. The carbodiimide may be used in an amount of about 1 to 700 molar equivalents based on maytansinol and, in many cases, is preferably employed in an amount not exceeding about 50 molar equivalents. The carbodiimide may be any compound having a carbodiimide bond (—N=C=N—) which will be transformed into a urea bond (—NH—CO—NH—) in the course of acylation reaction. Thus, it may be a compound of the following formula (III):

$R^1$—N=C=N—$R^2$   (III)

wherein $R^1$ and $R^2$ are organic residues which are capable of permitting the conversion of the carbodiimide portion into the corresponding urea in the course of said acylation reaction.

In the above formula (III), each of $R^1$ and $R^2$ may independently be a cycloalkyl group which may optionally have a di-lower-alkylamino group, a lower alkyl group which may optionally have a di-lower-alkylamino or morpholino group, or a phenyl group which may optionally have a lower alkyl group, for instance. For commercial purposes, the carbodiimide is preferably dicyclohexylcarbodiimide, although such other carbodiimides may also be employed as, for example, diphenylcarbodiimide, di-o-tolylcarbodiimide, di-p-tolylcarbodiimide, di-tert-butylcarbodiimide, 1-cyclohexyl-3-(2-morpholinoethyl)carbodiimide, 1-cyclohexyl-3-(4-diethylaminocyclohexyl)carbodiimide, 1-ethyl-3-(2-diethylaminopropyl)carbodiimide and 1-ethyl-3-(3-dimethylaminopropyl)carbodiimide.

This acylation reaction may be carried out in a suitable solvent. Examples of such solvent include esters (e.g. ethyl acetate, etc.), ethers (e.g. diethyl ether, dioxane, tetrahydrofuran, etc.), halogenated hydrocarbons (e.g. methylene chloride, chloroform, etc.), nitriles (e.g. acetonitrile, etc.), aromatic hydrocarbons (e.g. benzene, etc.), nitromethane, pyridine, dimethylformamide, dimethylsulfoxide, sulfolane, etc., as well as appropriate mixtures of such solvents.

This reaction may be carried out at a suitable temperature, normally from 0° C. to the reflux point of the reaction system.

The acylation reaction is desirably conducted in the presence of a catalyst which is able to promote the acylation of maytansinol. Examples of such catalyst include tertiary amines (such as aliphatic tertiary amines (e.g. triethylamine), and aromatic tertiary amines (e.g. pyridine, α-, β- or ν-picoline, 2,6-lutidine, 4-dimethyl aminopyridine, 4-(1-pyrrolidinyl)pyridine, dimethylaniline, diethylaniline, etc.)], although 4-dimethylaminopyridine and 4-(1-pyrrolidinyl)pyridine are especially desirable.

The acylation with said reactive derivative of carboxylic acid (II) may be carried out using a derivative of (II) which contains a functional group capable of acylating the 3-position of maytansinol, such as an acid anhydride of carboxylic acid (II). The solvent and catalyst for this reaction may be similar to those mentioned hereinbefore with reference to the acylation conducted in the presence of a carbodiimide. The reaction temperature is normally about −20° C. to +100° C. and, preferably, about +20° C. to +40° C., although the reaction may be hastened by heating the reaction system to a higher temperature.

The maytansinoid compound (I) produced by any of the above-described acylation processes can be isolated from the respective reaction mixtures by routine procedures such as concentration, solvent extraction, chromatography, recrystallization, etc.

The maytansinoid compounds (I) according to this invention have potent antimitotic and antitumor activities with comparatively low toxicity and are therefore suited for administration, oral or parenterally, to tumour-bearing warm-blooded animals (e.g. mouse, rat, rabbit, dog, cat and man) for the purpose of prolonging their survival times. Each compound (I) is normally administered in the form of a pharmaceutical preparation (e.g. injectable solution) as formulated with a carrier, diluent or the like which is known per se.

When compound (I) is administered in the form of an injectable preparation, it may be given subcutaneously, intraperitoneally, intravenously or intramuscularly, for instance. The dosage of compound (I) varies with the kind, symptom, administration route, etc. but, for example, in case of intravenous administration for prolonging life span of the animal suffering from leukemia or melanoma, it may be decided from the range of about 1 to 1000 μg/kg body weight, preferably about 10 to 500 μg/kg body weight, especially about 25 to 250 μg/kg body weight, per dose.

The injectable preparation can be prepared by the established pharmaceutical procedure; for example by dissolving about 50 μg to 3 mg of compound (I) in each about 0.5 ml of alcohol (e.g. ethanol), followed by addition of a sufficient amount of physiological saline to make a total of 10 ml. When a small dosage is indicated, the above solution may be further diluted with physiological saline.

The maytansinoid compounds (I) according to this invention are of value also in that they have antimicrobial activity, e.g. antifungal and antiprotozoal properties. Thus, for example, the maytansinoid compounds (I) are useful for treating *Tetrahymena pyriformis* W. As an antifungal or antiprotozoal agent, compound (I) is instrumental in assays of the bacterial flora of soil, active sludge, animal body fluids, etc. Thus, for the isolation of useful bacteria from soil samples or in the assay of activity of bacteria to the exclusion of those of protozoa and fungi in connection with the operation and analysis of active sludge systems for waste water treatment, the compound (I) can be advantageously employed to ensure selective growth of bacteria without permitting growth of the concomitant protozoa and fungi.

Thus, such a sample is added to a liquid or solid medium, and per milliliter of the inoculated medium, 0.1 ml of a 1% methanol-water solution of about 10 to 100 μg/ml of compound (I) is added, and then incubated to let the bacteria grow and multiply.

The maytansinoid compound (I), in an amount of 0.02 ml of a 1 mg/ml aqueous solution, is able to inhibit growth of causative microorganisms of stem rot (kogurokinkaku-byo), helminthosporium leaf rot (gomahagare-byo) and sheath blight (mongare-byo) in rice plants, for instance, and can therefore be used for the treatment of such plant diseases. The procedure may comprise dissolving compound (I) in 1% aqueous methanol to a concentration of about 0.5 to 5 μg/ml and spraying rice plants with the solution.

The starting compound maytansinol as used in the production of compounds (I) according to this invention is a known compound as a plant constituent [Kupchan et al., J. Amer. Chem. Soc. 97, 5294 (1975)] and can be also obtained by reductive cleavage of maytansine or its analogs.

Maytansinol may also be advantageously produced by cultivating an Antibiotic C-15003-producer of the genus Nocardia (FERM-P No. 3992, IFO-13726, ATCC-31281) in a culture medium to produce ansamytocin of the following formula (IV) in the culture broth and subjecting the same metabolite to reductive cleavage with a metal hydride such as LiAlH₄.[E. Higashide et al., Nature, Vol. 270, 721(1977) or U.S. Pat. No. 4,162,940 (Ser. No. 811,448)]

wherein $R^3$ is acetyl, propionyl, isobutyryl, n-butyryl or isovaleryl.

The following examples are intended to illustrate this invention in further detail and should be no means be construed as limiting the scope of the invention.

EXAMPLE 1

Maytansinol 3-cyclohexanecarboxylate

In 5 ml of dry dichloromethane are dissolved maytansinol (103.2 mg, 0.183 mmol) and cyclohexanecarboxylic acid (140 mg, 1.094 mmols), followed by addition of dicyclohexylcarbodiimide (DCC) (267 mg, 1.296 mmols). The mixture is stirred at room temperature for a while until insolubles have begun to separate out. Then, after addition of p-dimethylaminopyridine (DMAP) (50.8 mg, 0.416 mmol), the reaction mixture is stirred at room temperature overnight. The insolubles are filtered off, the filtrate is washed with 0.5 N HCl (ca. 10 ml) and saturated aqueous sodium hydrogen carbonate (ca. 10 ml) in that order and dried over anhydrous sodium sulfate. After the solvent is distilled off, the residue is chromatographed on a column of silica gel (75 g) and elution is carried out with ethyl acetate, the eluate being collected in 16-g fractions. Fractions 14 through 30 are pooled and the solvent is distilled off to recover 59 mg of crude product. This crude product is dissolved in ethyl acetate, followed by addition of ether, whereby 24.3 mg of maytansinol 3-cyclohexanecarboxylate is obtained as crystals melting at 202°–206° C. (decompn.)

NMR spectrum (CDCl$_3$) δ ppm: 0.85 (3H, s), 1.1–2.3 (10H,m), 1.24 (3H, d, J=6 Hz), 1.69 (3H, s), 2.16 (1H, dd, J=3 Hz and 15 Hz), 2.3–2.6 (1H, m), 2.57 (1H, dd, J=12 Hz & 15 Hz), 2.89 (1H, d, J=9 Hz), 3.13 (3H, s), 3.19 (1H, d, J=13 Hz), 3.36 (3H, s), ca 3.40 (1H, broad), 3.46 (1H, d, J=9 Hz), 3.48 (1H, d, J=13 Hz), 3.97 (3H, s), 4.25 (1H, m), 4.83 (1H, dd, J=3 Hz and 12 Hz), 5.47 (1H, dd, J=9 Hz and 15 Hz), 6.13 (1H, d, J=11 Hz), 6.32 (1H, s), 6.45 (1H, dd, J=11 Hz and 15 Hz), 6.84 (2H, s), etc.

UV spectrum ($\lambda_{max}^{MeOH}$)nm: 233, 240, 252.4, 281, 289.5

Mass spectrum (m/e) 674, 657, 631, 613, 598, 581, 578, 571, 543

In Examples 2 through 7, which appear below, the respective product compounds are obtainable by procedures analogous to those described in Example 1. In each of these Examples, the description proceeds in the order of: Example No. and the chemical name of product compound, followed by (1) the amount of maytansinol (mg); (2) the name of the corresponding carboxylic acid (its amount in mg); (3) the amount of DCC (mg); (4) the total amount of DMAP (mg); (5) yield of product compound (mg); (6) m.p. of product compound; (7) NMR spectrum of same (δ ppm, 90 MHz, in CDCl$_3$, TMS as internal reference), (8) UV spectrum of same ($\lambda_{max}^{MeOH}$ nm); (9) Mass spectrum (m/e) of same.

EXAMPLE 2

Maytansinol 3-cyclopropanecarboxylate (1) 100.0; (2) cyclopropanecarboxylic acid (91); (3) 264; (4) 63.2; (5) 16.1; (6) 182°–187° C. (decompn.); (7) 0.75–1.8 (5H, m), 0.85 (3H, s), 1.23 (3H, d, J=6 Hz), 1.70 (3H, s), 2.18 (1H, dd, J=3 Hz and 14 Hz), 2.56 (1H, dd, J=12 Hz and 14 Hz), 2.87 (1H, d, J=9 Hz), 3.18 (3H, s), 3.19 (1H, d, J=13 Hz), 3.36 (3H, s), ~3.40 (1H, broad), 3.47 (1H, d, J=9 Hz), 3.51 (1H, d, J=13 Hz), 3.98 (3H, s), 4.26 (1H, m), 4.81 (1H, dd, J=3 Hz and 12 Hz), 5.53 (1H, dd, J=9 Hz and 15 Hz), 6.10 (1H, d, J=11 Hz), ~6.30 (1H, s), 6.46 (1H, dd, J=11 Hz and 15 Hz), 6.84 (1H, d, J=1–2 Hz), 6.91 (1H, d, J=1–2 Hz), etc.; (8) 233, 241, 253, 281.5, 289.5; (9) 632, 615, 589, 571, 556, 539, 536, 529, 501.

EXAMPLE 3

Maytansinol 3-phenylacetate (1) 104.5; (2) phenylacetic acid (151.5); (3) 269.7; (4) 44.2; (5) 28.7; (6) 180°–182° C. (decompn.); (7) 0.86 (3H, s), 1.27 (3H, d, J=6 Hz), 1.69 (3H, s), 2.30 (1H, dd, J=3 Hz and 14 Hz), 2.50 (1H, dd, J=12 Hz and 14 Hz), 2.92 (1H, d, J=9 Hz), 3.00 (3H, s), 3.11 (1H, d, J=13 Hz), 3.38 (1H, d, J=13 Hz), 3.40 (3H, s), 3.49 (1H, d, J=9 Hz), an apparently AB-pattern absorption (~2H) centered at 3.72, 3.93 (3H, s), 4.29(m), 4.98 (1H, dd, J=3 Hz and 12 Hz), 5.69 (1H, dd, J=9 Hz and 15 Hz), 6.20 (1H, d, J=12 Hz), 6.49 (1H, dd, J=12 Hz and 15 Hz), 6.60 (1H, s), 6.83 (1H, s), 7.28 (5H, broads), etc.; (8) 233.5, 241 (sh), 253.5, 282, 289.5; (9) 621, 606, 589, 586, 579.

EXAMPLE 4

Maytansinol 3-benzoate (1) 102.2; (2) benzoic acid (134.6); (3) 266.6; (4) 88.8; (5) 13.3; (6) 174°–177° C. (decompn.); (7) 0.85 (3H, s), 1.30 (3H, d, J=6 Hz), 1.68 (3H, s), 2.31 (1H, dd, J=3 Hz and 15 Hz), 2.77 (1H, dd, J=12 Hz and 15 Hz), ~3.08 (1H, broad), 3.17 (3H, s), 3.19 (1H, d, J=13 Hz), 3.23 (3H, s), 3.32 (1H, d, J=9 Hz), 3.44 (1H, d, J=13 Hz), 3.98 (3H, s), 4.28 (1H, m), 4.77 (1H, dd, J=9 Hz and 15 Hz), 4.98 (1H, dd, J=3 Hz and 12 Hz), 5.80 (1H, d, J=11 Hz), 6.20 (1H, s), 6.28 (1H, dd, J=11 Hz and 15 Hz), 6.85 (1H, d, J=2 Hz), 7.09 (1H, d, J=2 Hz), 7.46–7.99 (3H, m), 7.87–8.17 (2H, m), etc.; (8) 232, 240(sh), 242.5, 281.5, 289; (9) 668, 625, 607, 592, 575, 572, 565.

EXAMPLE 5

Maytansinol 3-p-chlorobenzoate (1) 96.7; (2) p-chlorobenzoic acid (162.2); (3) 245.7; (4) 86.9; (5) 41.0; (6) 178°–183° C. (decompn.); (7) 0.85 (3H, s), 1.30 (3H, d, J=6 Hz), 1.70 (3H, s), 2.33 (1H, dd, J=3 Hz and 14 Hz), 2.77 (1H, dd, J=12 Hz and 14 Hz), 3.17 (3H, s), 3.27 (3H, s), 3.32 (1H, d, J=9 Hz), 3.45 (1H, d, J=13 Hz), 4.00 (3H, s), 4.26 (1H, m), 4.85 (1H, dd, J=9 Hz and 15 Hz), 5.00 (1H, dd, J=3 Hz and 12 Hz), 5.87 (1H, d, J=11 Hz), ~6.17 (1H, s), 6.32 (1H, dd, J=11 Hz and 15 Hz), 6.85 (1H, d, J=2 Hz), 6.95 (1H, d, J=2 Hz), 7.50 (2H, d, J=8 Hz), 8.00 (2H, d, J=8 Hz), etc.; (8) 238 (broad), 251, 282, 289(sh)

EXAMPLE 6

Maytansinol 3-(2-furan)carboxylate (1) 106.3; (2) 2-furancarboxylic acid (125.7); (3) 273.3; (4) 70.2; (5) 37.2; (6) 180°–189° C. (decompn.); (7) 0.82 (3H, s), 1.26 (3H, d, J=6 Hz), 1.67 (3H, s), 2.26 (1H, dd, J=3 Hz and 14 Hz), 2.71 (1H, dd, J=12 Hz and 14 Hz), 3.17 (3H, s), 3.26 (3H, s), 3.33 (1H, d, J=9 Hz), 3.51 (1H, d, J=13 Hz), 4.00 (3H, s), 4.30 (1H, m), 4.70 (1H, dd, J=9 Hz and 15 Hz), 4.80 (1H, dd, J=3 Hz and 12 Hz), 5.72 (1H, d, J=11 Hz), 6.29 (1H, dd, J=11 Hz and 15 Hz), 6.68 (1H, m), 6.84 (1H, d, J=2 Hz), 7.35 (1H, m), 7.53 (1H, d, J=2 Hz), 7.72 (1H, m), etc.; (8) 234, 244, 253, 281, 289,; (9) 615, 613, 597, 582, 565, 562, 555, 502.

EXAMPLE 7

Maytansinol 3-phenylpropionate (1) 101.0; (2) phenylpropionic acid (150.5); (3) 260; (4) 65.1; (5) 12; (6) 160°–162° C. (decompn.); (7) 0.88 (3H, s), 1.27 (3H, d, J=5 Hz), 1.65 (3H, s), 2.16 (1H, dd, J=3 Hz and 14 Hz), 2.51 (1H, dd, J=11 Hz and 14 Hz), ca. 2.6–3.4 (4H, m), 3.10 (3H, s), 3.13 (1H, d, J=13 Hz), 3.22 (3H, s), 3.45 (1H, d, J=13 Hz), 3.46 (1H, d, J=9 Hz), 3.95 (3H, s), 4.24 (1H, m), 4.90 (1H, dd, J=3 Hz and 11 Hz), 5.37 (1H, dd, J=9 Hz and 15 Hz), 6.00 (1H, d, J=10 Hz), 6.27 (1H, s), 6.39 (1H, dd, J=11 Hz and 15 Hz), 6.63 (1H, d, J=1–2 Hz), 6.78 (1H, d, J=1–2 Hz), 7.1–7.4 (5H, m), etc.; (9) 696, 635, 485, 470.

EXAMPLE 8

Maytansinol 3-nicotinate

In 10 ml of dry dichloromethane are dissolved maytansinol (114.4 mg, 0.2026 mmol) and nicotinic acid (150.2 mg, 1.22 mmols), followed by addition of DCC (301.6 mg, 1.465 mmols). The mixture is stirred at room temperature for ca. 20 minutes, after which DMAP (50.9 mg, 0.417 mmol) is added. The mixture is stirred at room temperature overnight. The insolubles are filtered off and the filtrate concentrated to dryness under reduced pressure. The residue is only partially soluble in 0.5 N-HCl. Therefore, it is made alkaline back with a saturated aqueous solution of sodium hydrogen carbonate, extracted with ethyl acetate and dried over anhydrous sodium sulfate. After the solvent is distilled off, the residue is chromatographed on a column of silica gel (75 g), elution being carried out with H$_2$O-saturated ethyl acetate (ca. 1.8 l). The eluate is collected in 16-g fractions and fractions 38 through 75 are pooled to recover 88.9 mg of crude product on removal of the solvent. This product is chromatographed for a second time on a column of silica gel (35 g) and elution is carried out with chloroform-methanol (40:1–30:1) (a total of 1.05 l), the eluate being collected in 16-g fractions. Fractions 21 through 40 are pooled and the solvent is distilled off to recover 65 mg of crude product. This crude product is further chromatographed on silica gel (40 g) and elution is carried out with ethyl acetate/$H_2O$-saturated ethyl acetate (2:1, V/V), the eluate being collected in 16-g fractions. Fractions 22 through 40 are pooled, the solvent distilled off and the residue dissolved in a small amount of ethyl acetate, followed by addition of ether. The resultant precipitate is recovered by filtration. By the above procedure is obtained 42.4 mg of maytansinol 3-nicotinate as white powders.

m.p. 184°–187° C. (decompn.)

NMR spectrum (in $CDCl_3$) δ: 0.90 (3H, s), 1.29 (3H, d, J=6 Hz), 1.69 (3H, s), 2.30 (1H, dd, J=3 Hz and 14 Hz), 2.76 (1H, dd, J=12 Hz and 14 Hz), 3.04 (1H, d, J=9 Hz), 3.15 (3H, s), 3.25 (3H, s), ~3.25 (1H, broad), 3.31 (1H, d, J=9 Hz), 3.60 (1H, d, J=13 Hz), 4.00 (1H, s), 4.21 (1H, m), 4.87 (1H, dd, J=9 Hz and 14 Hz), 5.18 (1H, dd, J=3 Hz and 12 Hz), 6.16 (1H, d, J=10 Hz), ~6.18 (1H, s), 6.34 (1H, dd, J=10 Hz and 14 Hz), 6.86 (1H, d, J=2 Hz), 6.96 (1H, d, J=2 Hz), 7.45 (1H, dd, J=5 Hz and 8 Hz), 8.32 (1H, m), 8.84 (1H, dd, J=2 Hz and 5 Hz), 9.28 (1H, d, J=2 Hz)

UV spectrum ($\lambda_{max}^{MeOH}$)nm: 223(sh), 232(sh), 240(sh), 252.5, 271(sh), 280, 289

Mass spectrum (m/e): 669, 626, 608, 593, 576, 573, 566

EXAMPLE 9

Maytansinol 3-picolinate

As in Example 8, maytansinol (109.0 mg, 0.193 mmol), picolic acid (144.2 mg, 1.171 mmols), DCC (278.5 mg, 1.352 mmols) and DMAP (50.2 mg, 0.411 mmol) are reacted in 10 ml of dry dichloromethane at room temperature for 6 hours. After the insolubles are filtered off, the filtrate is concentrated to dryness and the residue is dissolved in ethyl acetate, washed with water and dried over anhydrous sodium sulfate. The solvent is then distilled off. The residue is chromatographed on a column of silica gel (80 g) and elution is carried out with $H_2O$-saturated ethyl acetate, the eluate being collected in 16-g fractions. Fractions 24 through 49 are pooled and the solvent is distilled off to recover 98 mg of crude product. This crude product is chromatographed again on a column of silica gel (50 g), elution being carried out with chloroform-methanol (40:1, V/V). Fraction 18 through 33 (16 g each) are pooled, the solvent distilled off and the residue dissolved in ethyl acetate, followed by addition of ether. The resultant crystals are collected by filtration. By the above procedure is obtained 45.4 mg of maytansinol 3-picolinate. m.p. 190°–193° C. (decompn.)

NMR spectrum (in $CDCl_3$) δ: 0.84 (3H, s), 1.31 (3H, d, J=6 Hz), 1.64 (3H, s), 2.31 (1H, dd, J=3 Hz and 14 Hz), 2.78 (1H, dd, J=12 Hz and 14 Hz), 3.27 (1H, d, J=9 Hz), 3.17 (3H, s), 3.20 (3H, s), 3.40 (1H, d, J=9 Hz), 3.49 (1H, d, J=13 Hz), 3.99 (3H, s), 4.31 (1H, dd, J=9 Hz and 15 Hz), 4.36 (1H, m), 4.90 (1H, dd, J=3 Hz and 12 Hz), 5.41 (1H, d, J=11 Hz), ~6.20 (1H, s), 6.21 (1H, dd, J=11 Hz and 15 Hz), 6.83 (1H, d, J=2 Hz), 7.57 (1H, m), 7.90 (1H, m), 8.17 (1H, m), 8.35 (1H, d, J=2 Hz), 8.66 (1H, m), etc.

UV spectrum ($\lambda_{max}^{MeOH}$) nm: 231, 244, 253.2, 269.5(sh), 280, 289

Mass spectrum (m/e): 626, 608, 593, 576, 573, 566, 502

EXAMPLE 10

Maytansinol 3-isonicotinate

As in Example 8, maytansinol (98.4 mg, 0.174 mmol), isonicotinic acid (131.5 mg, 1.07 mmols), DCC (252.3 mg, 1.22 mmols) and DMAP (43.4 mg, 0.356 mmol) are reacted in 10 ml of dry dichloromethane at room temperature for 2 hours. The reaction mixture is then concentrated under reduced pressure, a small amount of ethyl acetate added to the residue, the insolubles filtered off, and the filtrate concentrated to dryness. The residue is chromatographed on silica gel (75 g) and elution is carried out with $H_2O$-saturated ethyl acetate (ca 2 l), the eluate being collected in 16-g fractions. Fractions 34 through 70 are pooled, the solvent distilled off and the residual crude product dissolved in a small amount of ethyl acetate. The solution is allowed to stand and the resultant crystals are recovered by filtration. By the above procedure is obtained 28.0 mg of maytansinol 3-isonicotinate as white crystals melting at 185°–187° C. (decompn.)

NMR spectrum (in $CDCl_3$) δ: 0.86 (3H, s), 1.29 (3H, d, J=6 Hz), 1.68 (3H, s), 2.33 (1H, dd, J=3 Hz and 15 Hz), 2.75 (1H, dd, J=12 Hz and 15 Hz), 3.17 (3H, s), 3.23 (1H, d, J=9 Hz), 3.24 (3H, s), 3.33 (1H, d, J=9 Hz), ~3.40 (1H, broad), 3.48 (1H, d, J=13 Hz), 3.98 (3H, s), 4.23 (1H, m), 4.84 (1H, dd, J=9 Hz and 15 Hz), 5.07 (1H, dd, J=3 Hz and 12 Hz), 5.86 (1H, d, J=11 Hz), ~6.18 (1H, s), 6.30 (1H, dd, J=11 Hz and 15 Hz), 6.85 (1H, d, J=2 Hz), 6.93 (1H, d, J=2 Hz), 7.86 (2H, m), 8.84 (2H, m), etc.

UV spectrum ($\lambda_{max}^{MeOH}$)nm: 233, 240(sh), 252.5, 281, 289

Mass Spectrum (m/e): 608, 593, 576, 573, 566, 502

EXAMPLE 11

Maytansinol 3-(N-acetyl)prolinate

In 10 ml of dry dichloromethane, there are admixed 97.0 mg (0.172 mmol) of maytansinol, 172.1 mg (1.034 mmols) of N-acetyl-L-proline, 251.4 mg (1.220 mmols) of DCC and 45.8 mg (0.375 mmol) of DMAP. The mixture is stirred at room temperature for 3 hours. The solvent is then distilled off, and the residue dissolved in a small amount of ethyl acetate. After the insolubles are filtered off, the filtrate is concentrated to dryness under reduced pressure, whereby 200.2 mg of crude product is obtained. This crude product is chromatographed on a column of silica gel (75 g) and elution is carried out with chloroform-methanol (500 ml of 60:1 (V/V), 400 ml of 50:1, 400 ml of 40:1, 600 ml of 30:1 and 500 ml of 20:1 in the order mentioned), the eluate being collected in 25-g fractions. Fractions 40 through 64 are pooled, the solvent is distilled off and about 52 mg of residue is chromatographed again on a column of silica gel (40 g) (solvent: $H_2O$-saturated ethyl acetate), the eluate being collected in 17-g fractions. Fractions 45 through 80 are pooled, the solvent distilled off and the residue dissolved in ethyl acetate, followed by addition of ether-hexane. The resultant precipitate is recovered by filtration. By the above procedure is obtained 22.2 mg of Compound A as white crystals. Of the fractions obtained in the first chromatography, fractions 89 through 130 are pooled, the solvent is distilled off and the residue (22.1 mg) purified by silica gel (12 g) chromatography (solvent: $H_2O$-saturated ethyl acetate). The fractions 15 through 30 are pooled and the solvent distilled off, whereupon 15.4 mg of Compound B is obtained as a glass-like product.

Based on the physical data presented hereinafter, it is clear that Compounds A and B are isomers of maytansinol 3-(N-acetyl)prolinate, being dissimilar only in respect of the steric orientation of the 2-position of proline.

COMPOUND A m.p. 195°–198° C. (decompn.)

NMR spectrum (in CDCl$_3$) δ ppm: 0.89 (3H, s), 1.28 (3H, d, J=6 Hz), 1.70 (3H, s), 2.17 (3H, s), 2.19 (1H, dd, J=3 Hz and 14 Hz), 2.65 (1H, dd, J=11 Hz and 14 Hz), 3.17 (3H, s), 3.33 (3H, s), 3.98 (3H, s), 4.36 (1H, m), ca 4.37 (1H, m), 4.90 (1H, dd, J=3 Hz and 11 Hz), 5.76 (1H, dd, J=9 Hz and 14 Hz), 6.14 (1H, d, J=11 Hz), ca. 6.35 (1H, s), 6.43 (1H, dd, J=11 Hz and 14 Hz), 6.73 (1H, d, J=ca. 1 Hz), 6.85 (1H, d, J=ca. 1 Hz), etc.

Mass spectrum (m/e): 642, 627, 485, 470, 450

UV spectrum (λ$_{max}^{MeOH}$)nm: 233, 243.5, 253.5, 282, 290

COMPOUND B

NMR spectrum (in CDCl$_3$) δ ppm: 0.88 (3H, s), 1.30 (3H, d, J=6 Hz), 1.72 (3H, s), 2.09 (3H, s), 2.15 (1H, dd, J=3 Hz and 14 Hz), 2.74 (1H, dd, J=11 Hz and 14 Hz), 3.19 (3H, s), 3.37 (3H, s), 3.97 (3H, s), ca. 4.25 (1H, m), 4.31 (1H, m), 4.90 (1H, dd, J=3 Hz and 11 Hz), 5.50 (1H, dd, J=10 Hz and 14 Hz), 6.25 (1H, d, J=10 Hz), ca. 6.27 (1H, s) 6.50 (1H, dd, J=10 Hz and 14 Hz), 6.80 (1H, d, J=ca. 1 Hz), 7.42 (1H, d, J=ca. 1 Hz)

Mass spectrum (m/e): 642, 627, 485, 470, 450

UV spectrum (λ$_{max}^{MeOH}$)nm: 233, 244, 253, 282, 290

EXAMPLE 12

Maytansinol 3-phenylacetate

In 3 ml of dry dichloromethane, there are admixed 50.7 mg (0.090 mmol) of maytansinol, 160.0 mg (0.630 mmol) of phenylacetic anhydride and 32.9 mg (0.270 mmol) of DMAP. The mixture is stirred at room temperature for 14 hours, at the end of which time it is washed with water. The solvent is distilled off and the residue is chromatographed on a column of silica gel (65 g) (solvent: ethyl acetate). The eluate is assayed by TLC and the fractions giving a spot at Rf above 0.45 are collected and the solvent distilled off. The residue is dissolved in ethyl acetate, and after addition of ether, seed crystals are added. The crystals thus obtained are collected by filtration. By the above procedure is obtained 11.5 mg of maytansinol 3-phenylacetate. In melting point and NMR spectrum, this product is identical with the product according to Example 3.

EXAMPLE 13

Maytansinol 3-(2-thiophene)carboxylate

In 5 ml of dry dichloromethane are dissolved 100.0 mg (0.177 mmol) of maytansinol and 136 mg (1.0625 mmols) of 2-thiophenecarboxylic acid, followed by addition of 255 mg (1.238 mmols) of DCC. The mixture is stirred at room temperature for a while. Then, following addition of 65 mg (0.533 mmol) of DMAP, the mixture is further stirred at room temperature for 13 hours. Then, 45 mg (0.352 mmol) of 2-thiophenecarboxylic acid, 85 mg (0.413 mmol) of DCC and 22 mg (0.180 mmol) of DMAP are further added. The mixture is stirred at the same temperature for 3 hours, after which the solvent is distilled off under reduced pressure. The residue is dissolved in a small amount of ethyl acetate, the insolubles filtered off and the filtrate chromatographed on a column (20 mm×48 cm) of silica gel (solvent system: ethyl acetate-H$_2$O-saturated ethyl acetate=3:1, V/V), the eluate being collected in 15-g fractions. Fractions 31 through 39 are pooled and the solvent distilled off. By the above procedure is obtained 30.0 mg of maytansinol 3-(2-thiophene)carboxylate as a glass-like solid. m.p.: 161°–163° C. (decompn.)

NMR spectrum (in CDCl$_3$) δppm: 0.82(3H, s), 1.28(3H, d, J=6 Hz), 1.66(3H, s), 2.29(1H, dd, J=4 Hz and 14 Hz), 2.72 (1H, dd, J=12 Hz & 14 Hz), 3.15(1H, d, J=13 Hz), 3.17(1H, d, J=9 Hz), 3.19(3H, s), 3.28(3H, s), 3.33(1H, d, J=9 Hz), 3.52 (1H, d, J=13 Hz), ca. 3.5(1H, broad), 3.98(3H, s), 4.30(1H, m), 4.67(1H, dd, J=9 Hz and 15 Hz), 4.81(1H, dd, J=4 Hz and 12 Hz), 5.95(1H, d, J=11 Hz), 6.28(1H, dd, J=11 and 15Hz), 6.49(1H, s), 6.84(1H, d, J=1.5 Hz), ca. 7.1(1H, m), 7.28(1H, d, J=1.5 Hz), ca. 7.6(1H, m), ca. 7.8(1H, m), etc.

Mass spectrum (m/e): 674, 631, 613, 503, 485, 470, 450

EXAMPLE 14

Maytansinol 3-(3,4,5-trimethoxyphenyl)acetate

As in Example 8, maytansinol (100 mg), 3,4,5-trimethoxyphenylacetic acid (239 mg), DCC (219 mg) and DMAP (47.2 mg) are reacted in 10 ml of dry dichloromethane at room temperature for 30 hrs. After the insolubles are filtered off, the filtrate is concentrated to dryness and the residue is dissolved in ethyl acetate, washed with water and dried over anhydrous sodium acetate. The solvent is then distilled off. The residue is chromatographed on a column of silica gel (25 g) with methanol/chloroform=1/100 V/V) to give 42 mg of maytansinol 3-(3,4,5-trimethoxyphenyl)acetate.

NMR spectrum (in CDCl$_3$) δ ppm: 0.78(s, 3H), 1.25(d, 3H), 1.63(s, 3H), 2.86(s, 3H), 3.33(s, 3H), 3.73(s, 3H), 3.85(s, 9H), 3.90(s, 2H), 7.17(s, 2H), etc.

Mass spectrum (m/e): 754(M$^+$−18), 711(M$^+$−61), 625, 485

EXAMPLE 15

Maytansinol 3-(3,4,5-trimethoxy)benzoate

As in the preceding Example 14, maytansinol (100 mg), 3,4,5-trimethoxybenzoic acid (224 mg), DCC(218 mg) and DMAP (47.2 mg) are reacted in 10 ml of dry dichloromethane at room temperature for 5 days. The reaction mixture is worked up as in Example 14 and the extracted crude product is chromatographed on a column of silica gel (25 g) with 5% methanol in chloroform to give 15 mg of maytansinol 3-(3,4,5-trimethoxy)benzoate.

NMR spectrum (in CDCl$_3$) δ ppm: 0.80(s, 3H), 1.23(d, 3H), 1.63(s, 3H), 3.23(broad, 6H), 3,90(2H), 3.96(s, 3H), 7.23(s, 1H), 7.30(s, 1H), etc.

MS(m/e): 758(M$^+$), 715, 697(M$^+$−61)

EXAMPLE 16

Maytansinol 3-(2-tert.butyl-tetrazol-5-yl)acetate

As in Example 8, maytansinol (113 mg), 2-tert.butyl-tetrazol-5-yl-acetic acid (184 mg), DCC (206 mg), and DMAP (49 mg) are reacted in 4 ml of dry dichloromethane at room temperature. The reaction mixture is worked up as in Example 14 and the crude product obtained is chromatographed on silica gel (50 g) with chloroform then 2% methanol-chloroform to give 95 mg of maytansinol 3-(2-tert.-butyl-tetrazol-5-yl)acetate.

NMR spectrum (in CDCl$_3$) δ ppm: 0.87(s, 3H), 1.23(d, 3H), 1.73(s, 9H), 3.10(s, 3H), 3.35(s, 3H), 3.97(s, 3H), 4.03(s, 2H), 6.82(d, 1H), 6.90(d, 1H).

EXPERIMENTAL DATA

Antitumor activity

Therapeutic tests were carried out in mice according to NCI-protocols 1,200 and 1,300, Cancer Chemother, Reports, Part 3, 1972, Vol. 3, No. 2, in which leukemia P-388 and melanoma B-16 tumor cells had been intraperitoneally transplanted, compound (I) being administered intraperitoneally once daily for 9 consecutive days. Life span prolongations obtained are shown in Table 1 as T/C % values.

TABLE 1

| | | Antitumor activities | |
|---|---|---|---|
| Compound | Dose (μg/kg) | P-388 (T/C %) | B-16 (T/C %) |
| Maytansinol 3-phenylacetate | 25 | 185 | 230 |
| | 12.5 | 164 | 207 |
| Maytansinol 3-cyclohexane carboxylate | 100 | | 193 |
| | 50 | | 188 |
| | 25 | | 193 |
| Maytansinol 3α-picolinate | 200 | | 173 |
| | 100 | 185 | 176 |
| | 50 | 193 | |

Antiprotozoal activity

Antiprotozoal activity of compound (I) was assayed with *Tetrahymena pyriformis* W as the test organism and a medium composed of 20 g tryptose-peptone (Difco Co.), 1 g yeast extract, 2 glucose, 1000 ml distilled water, 10 ml 1 M phosphate buffer (pH 7.0) as the assay medium. The microorganism was incubated at 28° C. for 44 to 48 hours and the growth inhibitory activity of compound (I) was assayed by the serial dilution method. The minimal inhibitory concentrations of compound (I) are shown in Table 2.

TABLE 2

| Compound | Antiprotozoal activity MIC (μg/ml) *Tetrahymena pyriformis* W |
|---|---|
| Maytansinol 3-phenylacetate | <2 |
| Maytansinol 3-cyclopropane carboxylate | 4 |
| Maytansinol 3-cyclohexane carboxylate | <2 |
| Maytansinol 3-benzoate | 4 |
| Maytansinol 3-(p-chloro)benzoate | ≧4 |
| Maytansinol 3-(3-phenyl)propionate | 2-4 |
| Maytansinol 3-(2-thiophene)carboxylate | ≧4 |
| Maytansinol 3-(2-furane)carboxylate | ≧4 |
| Maytansinol 3-α-picolinate | ≧4 |

EXAMPLES OF PHARMACEUTICAL COMPOSITIONS

Example A

Composition for Injection

| (1) Maytansinol 3-cyclohexanecarboxylate | 100 mg |
|---|---|
| (2) Ethanol | 10 g |
| (3) Polysorbate 80 (Tween 80) | 40 g |
| (4) Mannitol | 20 g |
| (5) Distilled water, a sufficient quantity to make | 1000 ml |

Preparation (1) is dissolved in (2). To this solution, (3) and (4) are added, followed by the addition of sterilized distilled water to make 1000 ml of the solution. Ten milliliter each of the solution is used to fill 100 amber ampoules and the air within the ampoules is replaced with nitrogen gas, then the ampoules is sealed. All the processes are conducted under sterile conditions.

Example B

Composition for Injection

| (1) Maytansinol 3-α-picolinate | 200 mg |
|---|---|
| (2) Ethanol | 5 g |
| (3) Polysorbate 80 (Tween 80) | 100 g |
| (4) Mannitol | 20 g |
| (5) Distilled water, a sufficient quantity to make | 1000 ml |

Preparation

By a similar procedure to that of Example A, an injectable solution of (1) is prepared.

What is claimed is:

1. A compound of the formula:

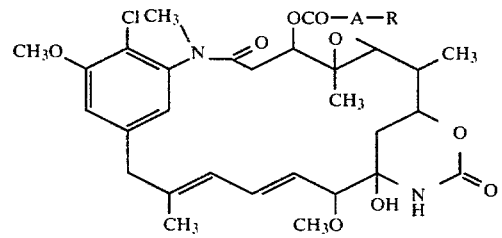

wherein

R is $C_{3-10}$ cycloalkyl, $C_{3-10}$ cycloalkenyl, phenyl or a heterocyclic group selected from the class consisting of pyridyl, pyrrolidinyl, tetrazolyl, furyl and thienyl, said cycloalkyl, cycloalkenyl, phenyl and heterocyclic group being unsubstituted or substituted by $C_{1-4}$ alkyl, $C_{1-4}$ alkoxy, $C_{2-4}$ alkanoyl, $C_{2-4}$ alkanoyloxy, $C_{2-4}$ alkoxycarbonyl, halogen, nitro, cyano, trifluoromethyl, di-$C_{1-4}$ alkylamino, $C_{1-4}$ alkylthio, methylsulfinyl, methylsulfonyl, oxo, thioxo or $C_{1-4}$ alkanoylamido, and A is $C_{1-4}$ alkylene or a bond, provided that A means said alkylene when attached to a N atom in said heterocyclic group R.

2. A compound according to claim 1, wherein R is $C_{3-7}$ cycloalkyl, phenyl, or heterocyclic group selected from the class consisting of pyridyl, pyrrolidinyl, tetrazolyl, furyl and thienyl, said cycloalkyl, phenyl and heterocyclic groups being unsubstituted or substituted by $C_{1-4}$ alkyl, $C_{1-4}$ alkoxy, $C_{2-4}$ alkanoyl or halogen.

3. A compound according to claim 1, wherein R is phenyl which is unsubstituted or substituted by $C_{1-4}$ alkoxy or halogen.

4. A compound according to claim 1, wherein R is pyridyl, pyrrolidinyl, tetrazolyl, furyl or thienyl, which is unsubstituted or substituted by $C_{1-4}$ alkyl or $C_{2-4}$ alkanoyl.

5. A compound according to claim 1, wherein R is $C_{3-7}$ cycloalkyl and A is a bond.

6. The compound according to claim 1, which is maytansinol 3-cyclohexanecarboxylate.

7. The compound according to claim 1, which is maytansinol 3-phenylacetate.

8. The compound according to claim 1, which is maytansinol 3-p-chlorobenzoate.

9. The compound according to claim 1, which is maytansinol 3-(2-furan)carboxylate.

10. The compound according to claim 1, which is maytansinol 3-picolinate.

11. The compound according to claim 1, which is maytansinol 3-(2-thiophene)carboxylate.

12. A pharmaceutical composition suitable for inhibiting the growth of tumour cells and prolonging the survival time of a warm-blooded animal which comprises as an active ingredient an effective amount of a compound of the following formula (I) and a pharmaceutically acceptable carrier or diluent therefor:

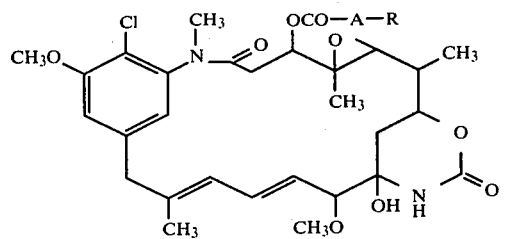

(I)

wherein
R is $C_{3-10}$ cycloalkyl, $C_{3-10}$ cycloalkenyl, phenyl or a heterocyclic group selected from the class consisting of pyridinyl, pyrrolidinyl, tetrazolyl, furyl and thienyl, said cycloalkyl, cycloalkenyl, phenyl and heterocyclic group being unsubstituted or substituted by $C_{1-4}$ alkyl, $C_{1-4}$ alkoxy, $C_{2-4}$ alkanoyl, $C_{2-4}$ alkanoyloxy, $C_{2-4}$ alkoxycarbonyl, halogen, nitro, cyano, trifluoromethyl, di-$C_{1-4}$ alkylamino, $C_{1-4}$ alkylthio, methylsulfinyl, methylsulfonyl, oxo, thioxo or $C_{1-4}$ alkanoylamido, and A is $C_{1-4}$ alkylene or a bond, provided that A means said alkylene when attached to a N atom in said heterocyclic group R.

13. A method for inhibiting the growth of tumour cells and prolonging the survival time of a tumour-bearing warm-blooded animal, which comprises administering to said animal an effective amount of a compound of the formula:

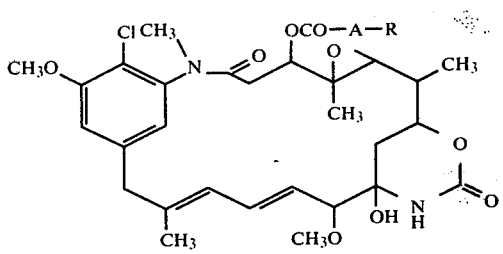

wherein
R is $C_{3-10}$ cycloalkyl, $C_{3-10}$ cycloalkenyl, phenyl or heterocyclic group selected from the class consisting of pyridyl, pyrrodinyl, tetrazolyl, furyl and thienyl, said cycloalkyl, cycloalkenyl, phenyl and heterocyclic group being unsubstituted or substituted by $C_{1-4}$ alkyl, $C_{1-4}$ alkoxy, $C_{2-4}$ alkanoyl, $C_{2-4}$ alkanoyloxy, $C_{2-4}$ alkoxycarbonyl, halogen, nitro, cyano trifluoromethyl, di-$C_{1-4}$ alkylamino, $C_{1-4}$ alkylthio, methylsulfinyl, methylsulfonyl, oxo, thioxo or $C_{1-4}$ alkanoylamido, and A is $C_{1-4}$ alkylene or a bond, provided that A means said alkylene when attached to a N atom in said heterocyclic group R.

* * * * *

UNITED STATES PATENT AND TRADEMARK OFFICE
CERTIFICATE OF CORRECTION

PATENT NO. : 4,248,870

DATED : February 3, 1981

INVENTOR(S) : Osamu MIYASHITA et al.

It is certified that error appears in the above—identified patent and that said Letters Patent is hereby corrected as shown below:

In headnote, after the filing date, insert ---[30] October 27, 1978 [JP]   Japan............133014---.

Signed and Sealed this

Nineteenth Day of May 1981

[SEAL]

Attest:

RENE D. TEGTMEYER

Attesting Officer     Acting Commissioner of Patents and Trademarks